United States Patent
Goto (10) Patent No.: US 8,262,677 B2
(45) Date of Patent: Sep. 11, 2012

(54) LIGATION TOOL FOR ENDOSCOPE AND ENDOSCOPIC LIGATION SYSTEM

(75) Inventor: Hiroaki Goto, Tokyo (JP)

(73) Assignee: Olympus Medical Systems Corp. (JP)

( * ) Notice: Subject to any disclaimer, the term of this patent is extended or adjusted under 35 U.S.C. 154(b) by 956 days.

(21) Appl. No.: 12/241,131

(22) Filed: Sep. 30, 2008

(65) Prior Publication Data

US 2009/0125037 A1 May 14, 2009

(30) Foreign Application Priority Data

Oct. 1, 2007 (JP) ................................ P2007-257212

(51) Int. Cl.
*A61B 17/10* (2006.01)
(52) U.S. Cl. ..................................................... 606/140
(58) Field of Classification Search ........... 606/139–144
See application file for complete search history.

(56) References Cited

U.S. PATENT DOCUMENTS

| | | | | |
|---|---|---|---|---|
| 5,100,419 A | * | 3/1992 | Ehlers | 606/140 |
| 5,269,789 A | * | 12/1993 | Chin et al. | 606/140 |
| 5,320,630 A | * | 6/1994 | Ahmed | 606/140 |
| 5,507,797 A | * | 4/1996 | Suzuki et al. | 606/140 |
| 5,624,453 A | * | 4/1997 | Ahmed | 606/140 |
| 5,697,940 A | * | 12/1997 | Chu et al. | 606/140 |
| RE36,629 E | * | 3/2000 | Zaslavsky et al. | 221/208 |
| 6,042,591 A | * | 3/2000 | Mears | 606/140 |
| 6,059,797 A | * | 5/2000 | Mears | 606/140 |
| 6,136,009 A | * | 10/2000 | Mears | 606/140 |
| 6,280,452 B1 | * | 8/2001 | Mears | 606/140 |
| 6,409,737 B1 | * | 6/2002 | Fortier et al. | 606/140 |
| 6,436,108 B1 | * | 8/2002 | Mears | 606/140 |
| 6,610,070 B1 | * | 8/2003 | Tolkoff | 606/140 |
| 2003/0171651 A1 | * | 9/2003 | Page et al. | 600/127 |

(Continued)

FOREIGN PATENT DOCUMENTS

EP 1 627 606 A2 2/2006

(Continued)

OTHER PUBLICATIONS

European Search Report dated Apr. 2, 2009 in counterpart European Patent Application No. 08017209.1-2310 (English language).

(Continued)

*Primary Examiner* — Melanie Tyson
*Assistant Examiner* — Son Dang
(74) *Attorney, Agent, or Firm* — Ostrolenk Faber LLP (57) ABSTRACT

A ligation tool for endoscope includes an overtube having an insertion lumen 21*a* made of a flexible material, which permits an insertion portion 11 of the endoscope to be inserted therethrough so as to advance and retreat, an O-ring 22 for ligation attached to a distal end of the overtube, and a operation wire 24 which is locked to the O-ring for ligation, has a distal portion extending to the proximal side of the overtube, and is operated to be pulled or pushed at its proximal side, thereby separating the O-ring for ligation from the tip of the overtube. According to this ligation tool for endoscope, time and effort taken to set the ligation tool for endoscope in the endoscope becomes unnecessary, a sufficient field of vision of the endoscope can be secured, and the curving performance of the tip of the insertion portion of the endoscope does not deteriorate. Furthermore, this ligation tool is also advantageous when endoscopic sclerotherapy is performed together.

14 Claims, 12 Drawing Sheets

U.S. PATENT DOCUMENTS

2004/0006256 A1* 1/2004 Suzuki et al. ............... 600/140

FOREIGN PATENT DOCUMENTS

| | | |
|---|---|---|
| JP | 11-514544 | 12/1999 |
| JP | 2000-102542 | 4/2000 |
| JP | 2000-511793 | 9/2000 |
| JP | 2001-353161 | 12/2001 |
| JP | 2002-017738 | 1/2002 |
| JP | 2005-323878 | 11/2005 |
| JP | 2005-537865 | 12/2005 |
| WO | WO 2004/021865 | 3/2004 |
| WO | WO 2008/127963 A1 | 10/2008 |

OTHER PUBLICATIONS

Letter from German associate dated Apr. 15, 2009 forwarding the European Search Report dated Apr. 2, 2009 to Japanese associate, including discussion of relevancy thereof (English language). German associate's letter dated Apr. 15, 2009 was date stamped received by Japanese associate on Apr. 20, 2009.

Japanese Office Action mailed May 23, 2012 in connection with corresponding Japanese Patent Application No. 2007-257212.

English translation of Japanese Office Action issued in connection with corresponding Japanese application provided as an explanation of prior art relevancy.

* cited by examiner

LIGATION TOOL FOR ENDOSCOPE AND ENDOSCOPIC LIGATION SYSTEM

BACKGROUND OF THE INVENTION

1. Field of the Invention

The present invention relates to a ligation tool for endoscope and an endoscopic ligation system which ligates a varix formed in a body tissue, such as in an esophagus or a stomach.

Priority is claimed on Japanese Patent Application No. 2007-257212, filed Oct. 1, 2007, the content of which is incorporated herein by reference.

2. Description of Related Art

Esophageal variceal ligation is known as a medical procedure for a varix formed in an esophagus or the stomach.

In this esophageal variceal ligation, after a varix is suctioned by a tubular cap mounted to the tip of an endoscope, an O-ring for ligation mounted at the cap in advance is removed and is hung on a root portion of the varix, and the varix is mechanically ligated and eradicated by the rubber force of the O-ring for ligation.

Meanwhile, conventionally, in order to perform the esophageal variceal ligation concretely, a ligation tool for endoscope in which a cap is attached to the tip of an insertion portion of an endoscope, O-rings for ligation are attached to an outer periphery of this cap, and a proximal portion of the operation wire which is locked to the O-rings for ligation and extends therefrom is operated to be pulled thereby separating an O-ring for ligation from the cap, is used (for example, refer to PCT Japanese Translation Patent Publication No. 2000-511793, and PCT Japanese Translation Patent Publication No. 11-514544).

SUMMARY OF THE INVENTION

A ligation tool for endoscope according to the invention includes a tubular body having an insertion lumen made of a flexible material, which permits an insertion portion of the endoscope to be inserted therethrough so as to advance and retreat, one or more O-rings for ligation attached to a distal end of the tubular body, and a separating mechanism which separates the O-ring for ligation from a tip of the tubular body.

According to the ligation tool for endoscope, the O-rings for ligation are attached to the tip of the tubular body separate from the endoscope. Thus, the operation for setting the ligation tool for endoscope in the endoscope is fundamentally unnecessary.

Furthermore, it is unnecessary to attach a member, such as a cap, to the tip of the insertion portion of the endoscope. In addition, the insertion portion of the endoscope can be advanced and retreated relative to the tubular body, and can be made to project forward from the tip of the tubular body. Therefore, the field of vision of the endoscope is not obstructed, and a sufficient field of vision can be secured.

Furthermore, as mentioned above, since a member, such as a cap, is not attached to the tip of the insertion portion of the endoscope, the curving property of the tip of the insertion portion of the endoscope does not deteriorate.

The ligation tool for endoscope according to the invention may include a fixing mechanism capable of axially fixing the tubular body to the insertion portion of the endoscope.

According to this ligation tool for endoscope, when the tubular body is not directly used, such as the case when the position of a varix is searched by the endoscope, this tubular body can be fixed to the insertion portion of the endoscope by the fixing mechanism. Therefore, the tubular body can be prevented from becoming obstructive.

In the ligation tool for endoscope according to the invention, the fixing mechanism may fix the tubular body to a predetermined position of the insertion portion of the endoscope in advance.

According to this ligation tool for endoscope, for example, the fixed position of the tubular body relative to the insertion portion of the endoscope by the fixing mechanism can be determined such that the ligation tool is brought into any of a state where the O-ring for ligation attached to the distal end of the tubular body does not come within the field of vision of the endoscope, a state where the distal end of the endoscope is made to project further forward from the distal end of the tubular body, and a state where the distal end of the tubular body is made to project further forward from the distal end of the endoscope so that a varix can be suctioned by the distal end of the tubular body. This makes it possible to smoothly perform medical procedure.

In the ligation tool for endoscope according to the invention, the separating mechanism may include an operation wire which is locked to the O-ring for ligation at its distal side, and is operated to be pulled or pushed at its proximal side, thereby separating the O-ring for ligation from the tip of the tubular body.

According to this ligation tool for endoscope, the operation wire can be inserted between the tubular body and the insertion portion of the endoscope. In this case, since the channels of the endoscope are not used, the channels can be utilized for permitting an injection needle for the injection of a sclerosing agent to be inserted therethrough. The ligation tool is effective when the endoscopic sclerotherapy is performed together.

In the ligation tool for endoscope according to the invention, the length of the tubular body may be set to be shorter than the length of the insertion portion of the endoscope.

According to this ligation tool for endoscope, even when the tip of the tubular body and the tip of the insertion portion of the endoscope are aligned so as to be almost in the same position in their length direction, a proximal portion of the insertion portion of the endoscope protrudes from a proximal portion of the tubular body, and is exposed to the outside. As a result, since the proximal portion of the insertion portion of the endoscope does not interfere with the tubular body, smooth operation of the endoscope is possible.

In the ligation tool for endoscope according to the invention, a seal portion may be provided to air-tightly partition a space formed between the tubular body, and the insertion portion of the endoscope into a distal space and a proximal space.

According to this ligation tool for endoscope, when a varix is suctioned by the tip of the tubular body, a negative pressure space can be made small. For this reason, a suction source with a small capacity is satisfactorily used as a suction source of an air suction apparatus, and the time required for suction can also be shortened.

In the ligation tool for endoscope according to the invention, the seal portion may be provided between the distal end of the tubular body, and a distal end of the insertion portion of the endoscope.

According to this ligation tool for endoscope, the negative pressure space for suction of a varix formed closer to the distal side than the seal portion can be set more narrowly. For this reason, a suction source with smaller capacity is satisfactorily used as a suction source of an air suction mechanism, and the time required for suction can also be further shortened.

In the ligation tool for endoscope according to the invention, a proximal portion of the operation wire may be connected to a wire operation portion which pulls or pushes the operation wire, and the wire operation portion may be detachably attached to an endoscope control portion.

According to this ligation tool for endoscope, when the wire operation portion of the ligation tool for endoscope is attached to the endoscope control portion, it becomes easy for an operator to handle the wire operation portion. Furthermore, when the wire operation portion of the ligation tool for endoscope is detached from the endoscope control portion, it becomes easy for a helper to handle the wire operation portion. As a result, the position of the wire operation portion of the ligation tool for endoscope can be freely selected according to the form of esophageal variceal ligation.

An endoscopic ligation system includes the above ligation tool for endoscope according to the invention, and an endoscope in which an insertion portion is inserted through an insertion lumen of the tubular body so as to advance and retreat.

According to this endoscopic ligation system, the same operation effects as the operation effects obtained by the ligation tool for endoscope are exhibited.

DETAILED DESCRIPTION OF THE INVENTION

Hereinafter, an embodiment of the invention will be described with reference to the accompanying drawings.

Figure 1:
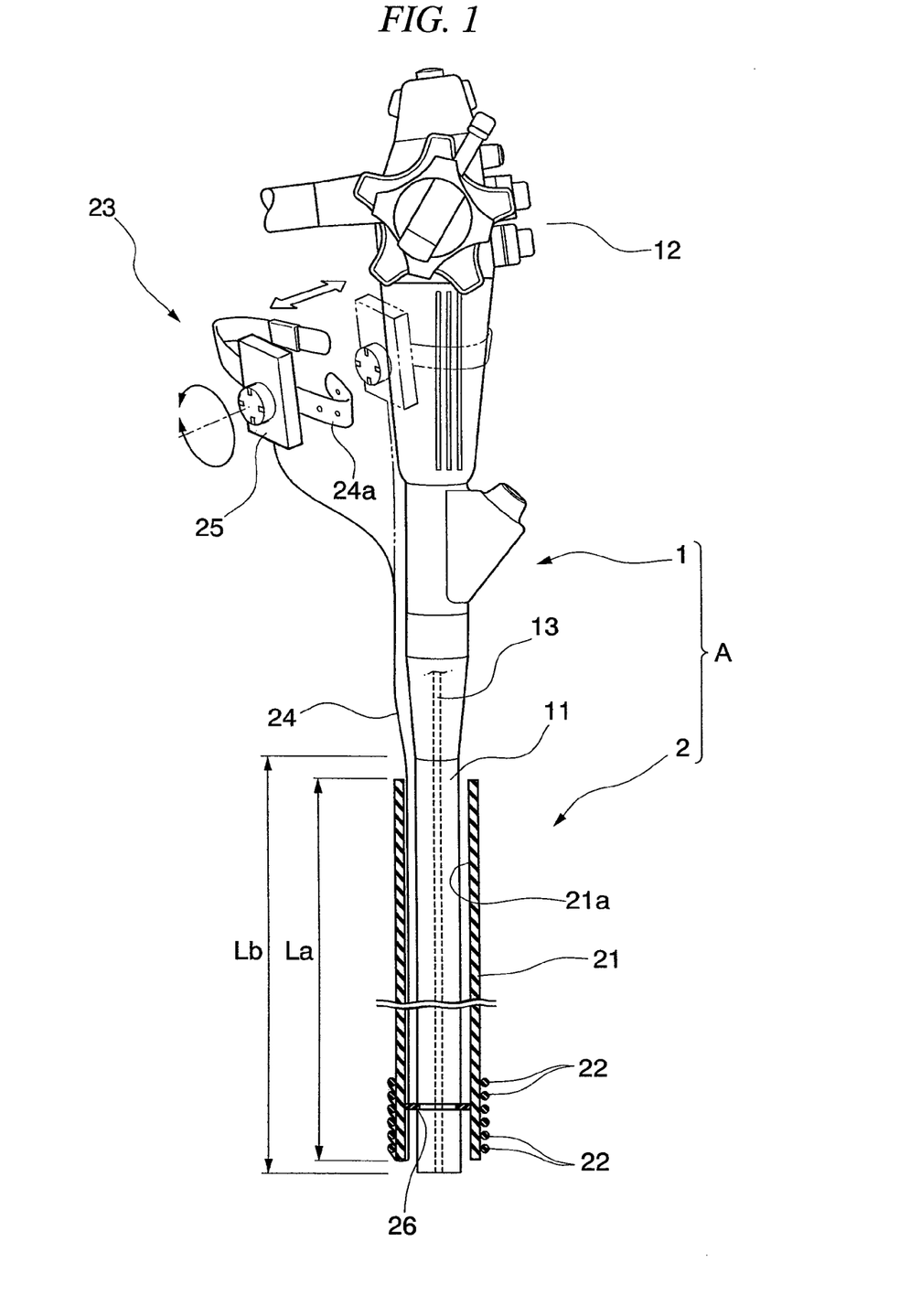
FIG. 1 is a configuration view of an endoscopic ligation system showing an embodiment of the invention.
Figure 2:
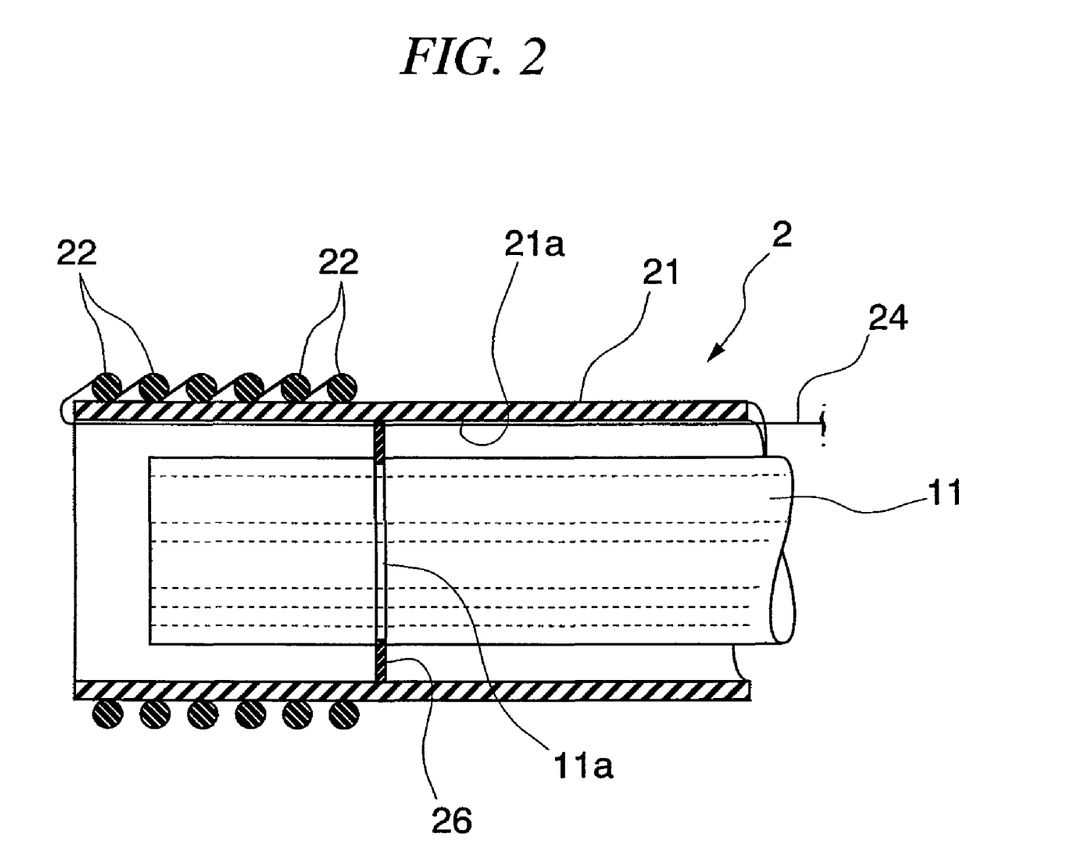
FIG. 2 is a sectional view showing chief parts of a ligation tool for endoscope.

FIG. 1 to FIG. 6 show the embodiment of the invention, FIG. 1 is a configuration view of an endoscopic ligation system, and FIG. 2 is a sectional view showing chief parts of a ligation tool for endoscope.

As shown in FIG. 1, the endoscopic ligation system A is obtained by combining an endoscope 1 and a ligation tool for endoscope 2.

The endoscope 1 includes an insertion portion 11 having flexibility, an endoscope control portion 12 which is connected to a proximal end of the insertion portion 11 to bend and control a tip of the insertion portion 11, a plurality of channels 13 which is formed through the inside of the insertion portion 11, and permits forceps, etc. to be inserted therethrough.

The ligation tool for endoscope 2 includes an overtube 21 which permits the insertion portion 11 of the endoscope 1 to be inserted therethrough so as to advance and retreat, one or more O-rings 22 for ligation which are attached to a outer periphery of the distal end of the overtube 21 (refer to the FIG. 2), and a separating mechanism 23 which permits the O-rings 22 for ligation to be separated from a tip of the overtube 21. Here, in the example of FIGS. 1 and 2, the separating mechanism 23 includes a operation wire 24 which distal portion is locked to the O-rings 22 for ligation and whose proximal portion extends to the proximal side of the overtube 21, and a wire operation portion 25 which is attached to the proximal side of the operation wire 24 and pulls the operation wire 24 for the operation. (In addition, the separating mechanism is not limited to the wire)

Furthermore, an air suction mechanism (not shown) is attached to the endoscope so that air can be suctioned from the tip of a channel of the endoscope.

The overtube 21 is formed in a tubular shape so as to have an insertion lumen 21a which permits the insertion portion 11 of the endoscope to be inserted therethrough. The optical member 21 is fabricated of optical glass. Furthermore, the length La of the overtube 21 is set to be shorter than the length Lb of the insertion portion 11 of the endoscope 1.

A ring-shaped seal portion 26 is interposed between the overtube 21, and the insertion portion 11 of the endoscope. A space formed between the overtube 21, and the insertion portion 11 of the endoscope, is airtightly partitioned into a distal portion and a proximal portion by the seal portion 26. The seal portion 26 has suitable elasticity, air-tightly abuts on an inner peripheral surface of the overtube 21, and an outer peripheral surface of the insertion portion 11 of the endoscope, and permits axial movement of the overtube 21 relative to the insertion portion 11 and the seal portion 26.

In addition, in the example shown in FIG. 2, the outer periphery of the distal end of the insertion portion 11 is provided with a ring groove 11a for mounting the seal portion 26. The ring groove 11a is not necessarily a required portion. For example, the ring groove 11a may be dispensed when a fixing force to the outer periphery of the insertion portion 11 is sufficiently obtained by the frictional force of the seal portion 26.

The O-rings 22 for ligation have an elastic force required to ligate a varix, and is made of a material which is harmless to a human body, for example, natural rubber or a soft plastic material. Furthermore, in the example shown in FIG. 2, the O-rings 22 for ligation are set at the outer periphery of the distal end of the overtube 21. However, the invention is not limited thereto. For example, the O-rings may be set in a groove formed inside the overtube 21 by thickening the overtube, or the number of O-rings is not limited to a plurality of pieces, or may be one.

The operation wire 24 has a strength such that the force which separates the O-rings 22 for ligation from the overtube 21 can be transmitted when the operation wire 24 is pulled for the operation, and is made of a material which is harmless to a human body. In the example shown in FIG. 1, the operation wire 24 passes between the insertion portion 11 of the endoscope, and the overtube 21. However, the invention is not limited thereto. For example, the operation wire may pass through the outside of the overtube 21 or may pass through the inside of the channels 13 of the insertion portion 11.

Furthermore, the operation wire 24 is one in the example shown in FIGS. 1 and 2, and its tip and intermediate portion are locked to the plurality of O-rings 22 for ligation. However, the invention is not limited thereto. For example, separate operation wires 24 may be locked to a plurality of rings 22 for ligation, and a plurality of operation wires may be locked to one O-ring 22 for ligation. Furthermore, the operation wire may be one at its proximal side, may be branched on the way, and may be a plurality of pieces at its distal side, and the distal portion branched into multiple pieces may be locked to the O-rings 22 for ligation.

In addition, a well-known technique is used as a concrete aspect in which the operation wire 24 is locked to the O-rings 22 for ligation.

The wire operation portion 25 is detachably attached to the endoscope control portion 12. As an attachment method of the wire operation portion 25 to the endoscope control portion 12, it is considered that a band 25a attached to the wire operation portion 25 is utilized as shown in FIG. 1, mutually corresponding concavo-convex portions provided in a casing for the wire operation portion 25 and a casing for the endoscope control portion 12, respectively, are fitted together, or a surface fastener is used. Furthermore, the wire operation portion 25 may be attached in such a manner that a portion thereof is inserted into the channels 13 of the endoscope.

Figure 3:
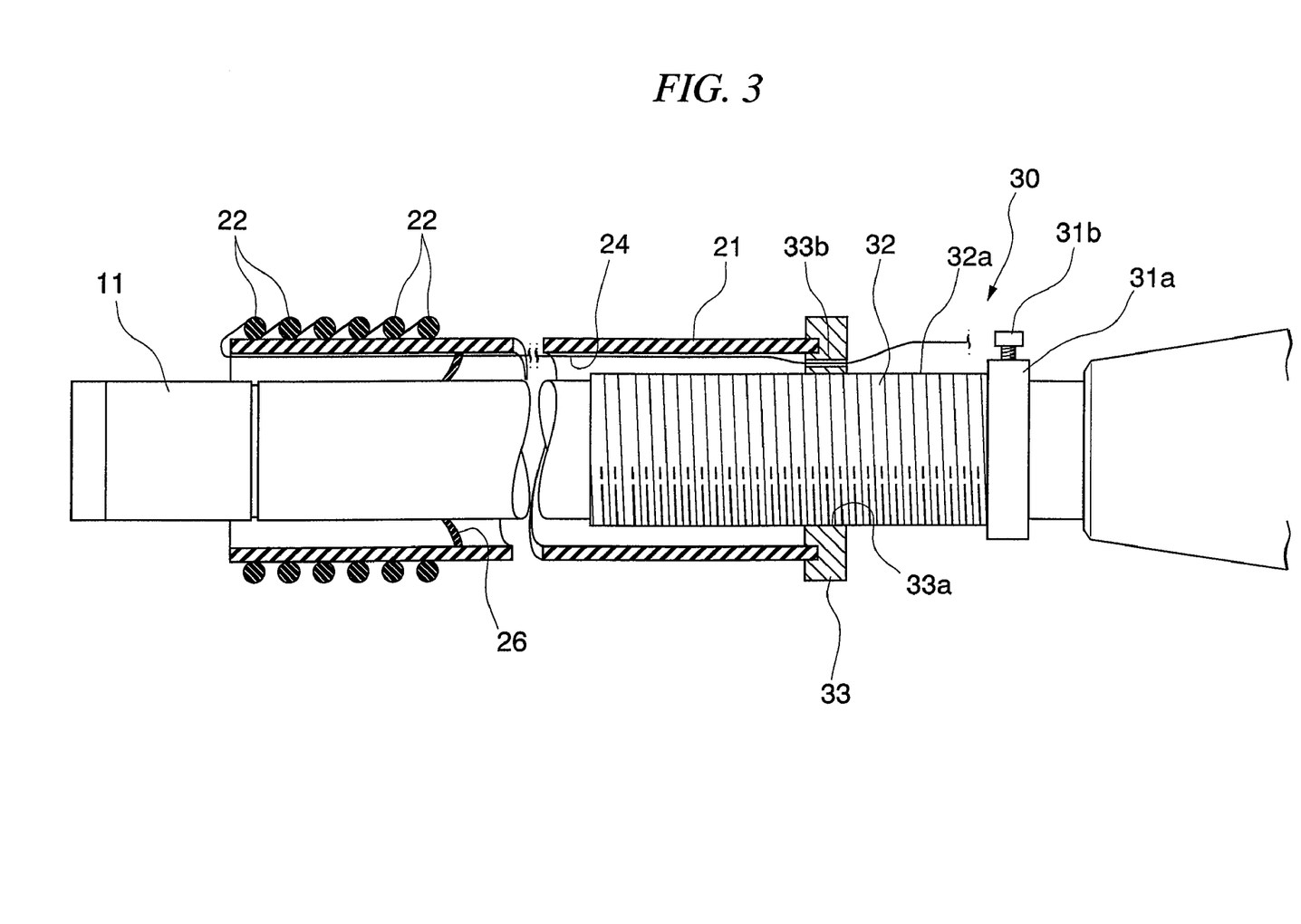
FIG. 3 is a side view obtained when a portion showing a fixing mechanism of the embodiment of the invention is sectioned.
Figure 4:
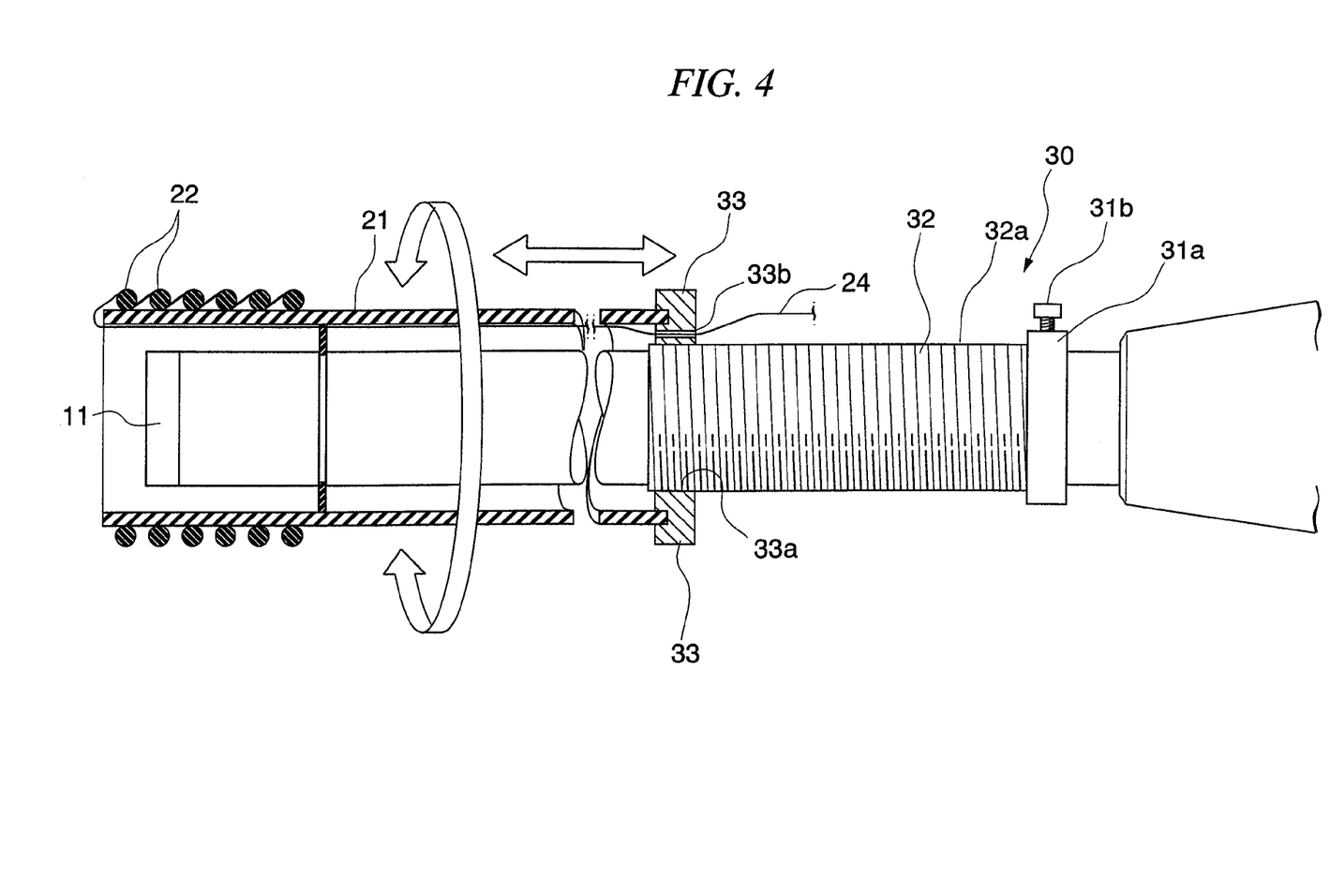
FIG. 4 is a side view obtained when a portion showing the operation of the fixing mechanism of the embodiment of the invention is sectioned.

As shown in FIGS. 3 and 4, a fixing mechanism 30 which allows axial fixation of the overtube 21 to the insertion portion 11 of the endoscope is provided between the insertion portion 11 of the endoscope, and the overtube 21.

The fixing mechanism 30 includes a cylindrical inner connector 32 to which a fixing ring 31a is fixed by, for example, a locking screw 31b, and a ring portion 33 which have a female thread portion 33a screwed to a male thread portion 32a formed at the outer periphery of the inner connector 32, at the outer periphery of the proximal side of the insertion portion 11. The ring portion 33 is fixed to a proximal end of the overtube 21 by a suitable fixing means, such as an adhesive or welding. For this reason, as shown in FIG. 4, a longitudinal fixed position of the overtube to the insertion portion can be arbitrarily changed by rotating the ring portion 33 integrally with the overtube 21.

In addition, marks, such as partition lines or color coding, are given to the male thread portion 32a formed at the outer periphery of the inner connector 32. This enables a longitudinal fixed position of the overtube 21 to the inner connector 32, in other words, a longitudinal fixed position of the overtube 21 to the insertion portion 11 to which an interconnector 32 is fixed to be fixed in a preset position.

Figure 5:
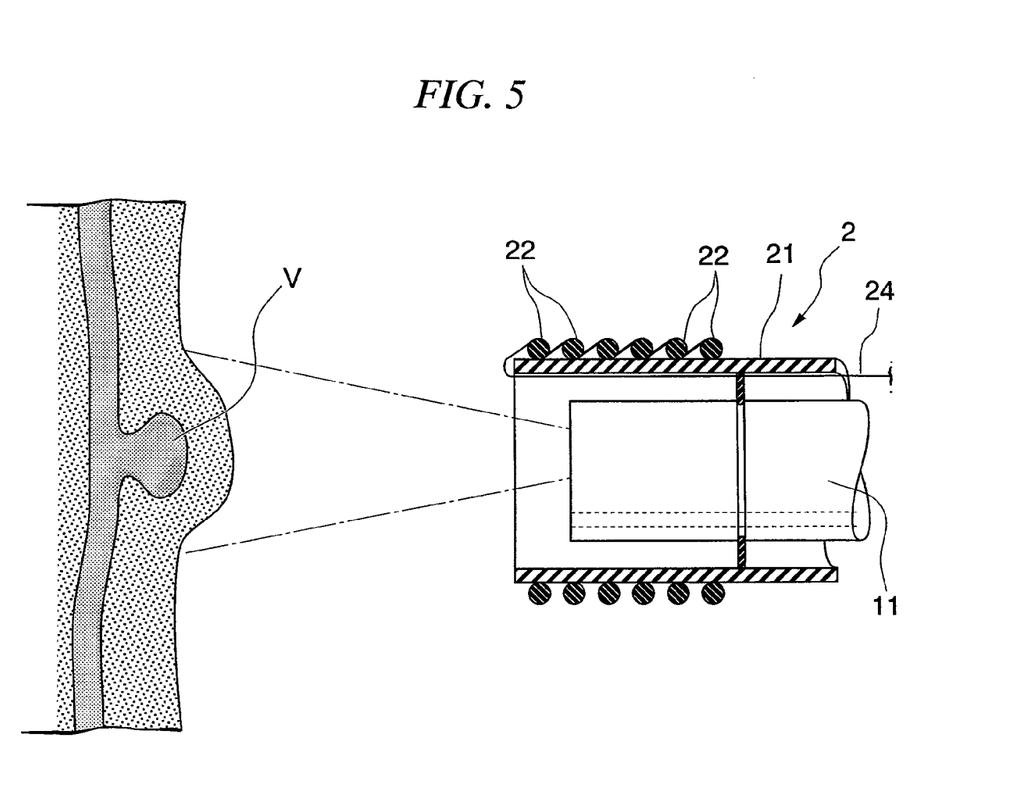
FIG. 5 is a sectional view showing a sequence when a varix is ligated by the endoscopic ligation system.
Figure 6:
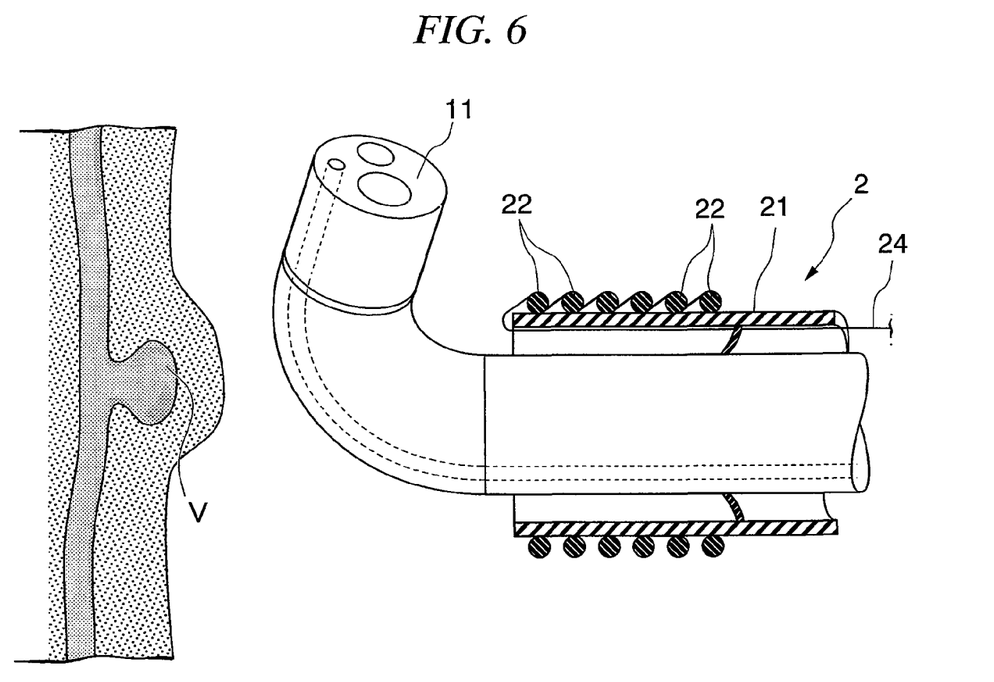
FIG. 6 is a sectional view showing another example when a varix is ligated by the endoscopic ligation system.
Figure 7:
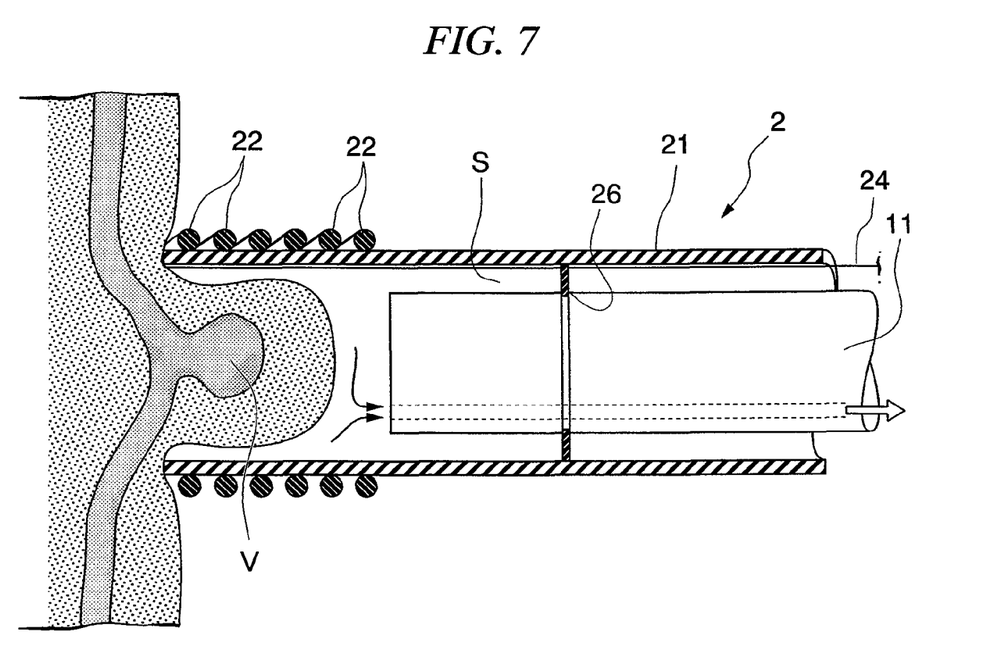
FIG. 7 is a sectional view showing a sequence when a varix is ligated by the endoscopic ligation system.

Here, examples of the preset position include a position where the tip of the overtube protrudes slightly further than the tip of the insertion portion of the endoscope as shown in FIG. 5, and the O-rings for ligation which is attached to the overtube does not come within the field of vision at the tip of the insertion portion; a position where the tip of the overtube retreats more than the tip of the insertion portion of the endoscope, and does not interfere with a curved portion of the tip of the insertion portion as shown in FIG. 6; and a position where the tip of the overtube protrudes more than the tip of the insertion portion of the endoscope, and which is suitable for suction of the varix V as shown in FIG. 7.

Next, the operation of the ligation tool for endoscope 2 and endoscopic ligation system A of the above configuration will be described.

The O-rings 22 for ligation are set at the outer periphery of the distal end of the overtube 21 in advance, and the operation wire 24 is locked to the O-rings 22 for ligation in advance.

When esophageal variceal ligation is performed, the insertion portion 11 of the endoscope is first inserted into and set in the overtube 21. At this time, the operation wire 24 passes, for example, between the insertion portion 11 of the endoscope, and the overtube 21, and is drawn out from a small hole 33b formed in the ring portion 33 at the proximal side the overtube 21. In this state, the tip of the insertion portion 11 of the endoscope 1 and the tip of the overtube 21 are inserted into a body orally while an image is observed through a camera of the endoscope.

At this time, when the overtube 21 obstructs the field of vision of the endoscope 1 and the front is not easily seen, the ring portion 33 is rotated integrally with the overtube 21, thereby permitting the overtube 21 to retreat to the proximal side relative to the insertion portion 11 of the endoscope 1 as shown in FIG. 5 so that the tip of the overtube 21 or the O-rings 22 for ligation may be kept from coming within the field of vision of the endoscope. Furthermore, when the overtube 21 interferes with the curved portion of the tip of the insertion portion 11, and thereby, the curved portion is not easily curved, the ring portion 33 can be rotated integrally with the overtube 21, thereby permitting the tip of the overtube 21 to retreat greatly from the tip of the insertion portion as shown in FIG. 6 so as not to interfere with the curved portion.

In this way, the insertion portion 11 of the endoscope 1 is inserted into an esophagus, and is moved to a position in the vicinity of the varix V. Next, a tip face of the insertion portion 11 and a tip opening of the overtube 21 are made to face the varix V while the endoscope control portion 12 is operated, and the tip of the insertion portion 11 is curved (refer to FIG. 5).

Then, the overtube 21 is slightly advanced to secure a space sufficient to suction the varix V between the tip of the overtube 21 and the tip face of the insertion portion 11.

In this state, the tip of the overtube 21 is pressed against a tissue in the body.

At this time, as shown in FIG. 7, an enclosed space S which is surrounded by the tissue in the body, the overtube 21, the insertion portion 11 of the endoscope, and the seal portion 26 is formed.

Then, air is suctioned from the space S via the channels 13 of the insertion portion 11, by the operation of the air suction mechanism which is not shown, and the space S is brought into negative pressure. Along with this, the varix V is suctioned into the space S.

Figure 8:
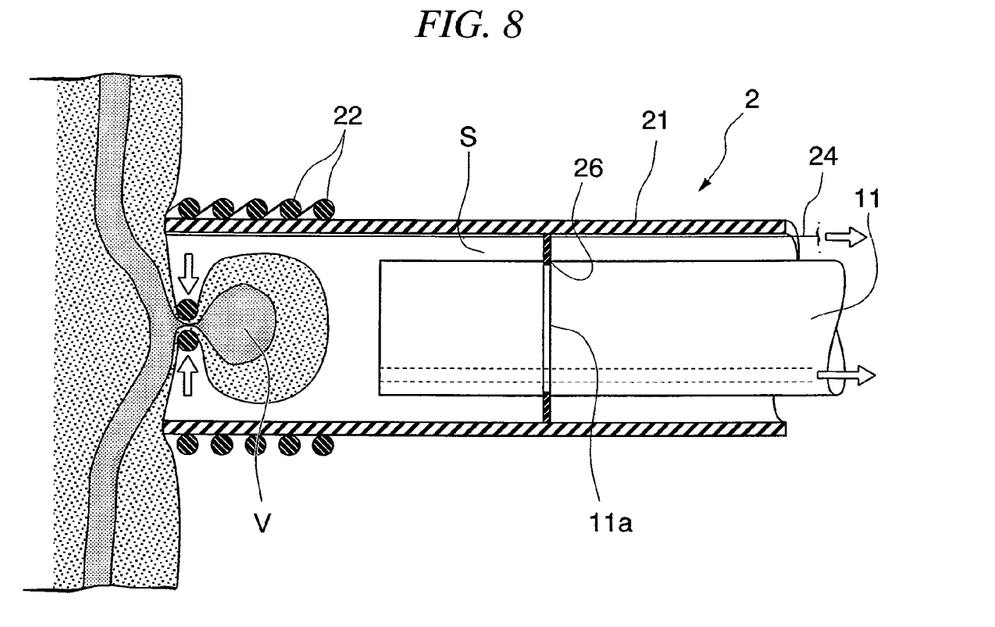
FIG. 8 is a sectional view showing another example when a varix is ligated by the endoscopic ligation system.

Subsequently, the wire operation portion 25 is operated so as to pull the operation wire 24, and only the O-ring 22 for ligation which exists at the tip is separated from the overtube 21. Then, as shown in FIG. 8, the separated O-ring 22 for ligation is hung on a root portion of the varix V, thereby litigating the varix V.

Next, the suction of air from the space S by the air suction mechanism is stopped, the insertion portion 11 of the overtube 21 and the endoscope are pulled back toward the hand side of the operator, and the opening tip of the overtube 21 is separated from the ligated varix V.

In the case where other varice V is ligated, operations after the operation of identifying the position of the varix V with the endoscope are repeated while the overtube 21 and the insertion portion 11 of the endoscope are inserted into the body.

According to the ligation tool for endoscope 2 and the endoscopic ligation system A, the O-rings 22 for ligation are attached to the tip of the overtube 21 which is a member separate from the endoscope 1. Thus, the operation for setting the ligation tool for endoscope 2 in the endoscope 1 is fundamentally unnecessary.

Furthermore, it is unnecessary to attach a member, such as a cap, to the tip of the insertion portion 11 of the endoscope. In addition, the insertion portion 11 of the endoscope can be advanced and retreated relative to the overtube 21, and can be made to project forward from the tip of the overtube 21. Therefore, the field of vision of the endoscope is not obstructed by the overtube 21, and a sufficient field of vision can be secured.

Furthermore, as mentioned above, since a member, such as a cap, is not attached to the tip of the insertion portion 11 of the endoscope, the curving property of the tip of the insertion portion 11 of the endoscope does not deteriorate.

Figure 9:
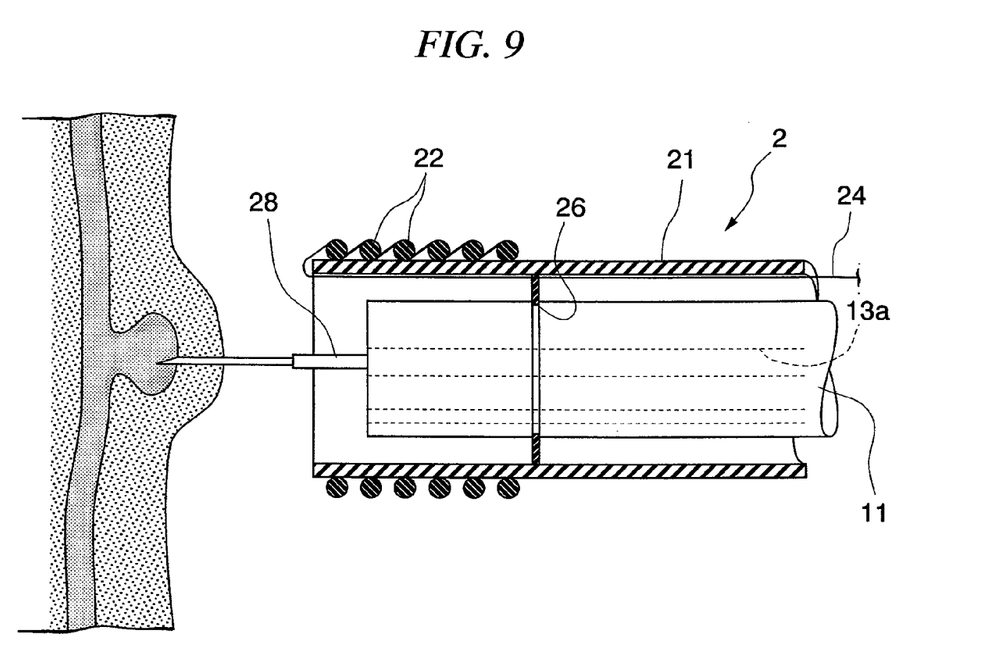
FIG. 9 is a sectional view showing another example when a varix is ligated by the endoscopic ligation system.

Furthermore, the operation wire 24 can be inserted between the insertion portion 11 of the endoscope, and the overtube 21. Accordingly, the channels of the endoscope are not used for insertion of the operation wire. Therefore, as shown in FIG. 9, the channels 13a which are separate from air suction can be utilized as a passage for permitting an injection needle 28 for injecting a sclerosing agent to be inserted therethrough. As a result, it is possible to perform endoscopic sclerotherapy together with esophageal variceal ligation.

Furthermore, in the ligation tool for endoscope 2, the seal portion 26 is provided between the insertion portion 11 of the endoscope, and the overtube 21. Thus, when the varix V is suctioned by the tip of the overtube, the negative pressure space S for suctioning the varix V can be made small. For this reason, a suction source with small capacity is satisfactorily used as a suction source of an air suction apparatus, and the time required for suction can also be shortened. However, the seal portion 26 is not limited to the arrangement at the tip of the insertion portion 11 as shown, and may be arranged in the vicinity of an operator (hand side of the operator).

Furthermore, in the ligation tool for endoscope 2, the wire operation portion 25 which pulls the operation wire 24 is detachably attached to the endoscope control portion 12. As a result, when the wire operation portion 25 is attached to the endoscope control portion 12 as indicated by chain double-dashed line in FIG. 1, the wire operation portion 25 can be fixed in the vicinity of the endoscope control portion. Therefore, it becomes easy for an operator who performs esophageal variceal ligation to handle the wire operation portion 25. On the other hand, when the wire operation portion 25 is detached from the endoscope control portion 12, it becomes easy for a helper to handle the wire operation portion 25. Thus, the position of the wire operation portion 25 of the ligation tool for endoscope can be freely selected according to the form of esophageal variceal ligation.

In addition, the invention is not limited to the above embodiment, but suitable design changes can be made without departing from the spirit and scope of the invention.

For example, in the above embodiment, the channels 13 of the insertion portion 11 are utilized as air passages when the varix V is drawn into the space S partitioned by the tip face of the insertion portion 11 of the endoscope, the overtube 21, etc. However, the invention is not limited thereto. For example, the clearance between the insertion portion of the endoscope, and the overtube can be utilized as an air passage. In this case, the seal portion 26 becomes unnecessary.

Furthermore, in the above embodiment, the operation wire 24 is pulled in order to separate the O-rings 22 for ligation from the overtube 21. However, the invention is not limited thereto. For example, the O-rings 22 for ligation may be separated from the overtube 21 by pushing out and operating the operation wire 24.

Furthermore, the tip shape of the overtube 21 is not limited to a shape which is cut so as to be orthogonal to the axial direction, but may be a shape which is obliquely cut with respect to the axial direction.

Furthermore, the portion of the overtube 21 which covers an endoscope angle may be made of a flexible material so that there may be no hindrance to angle operation.

Furthermore, although the case where the varix V of an esophagus is ligated has been described as an example in the above embodiment, the invention is not limited thereto, and the invention can also be applied to a case where varices in other parts in a living body are ligated.

[Modification]

Figure 10:
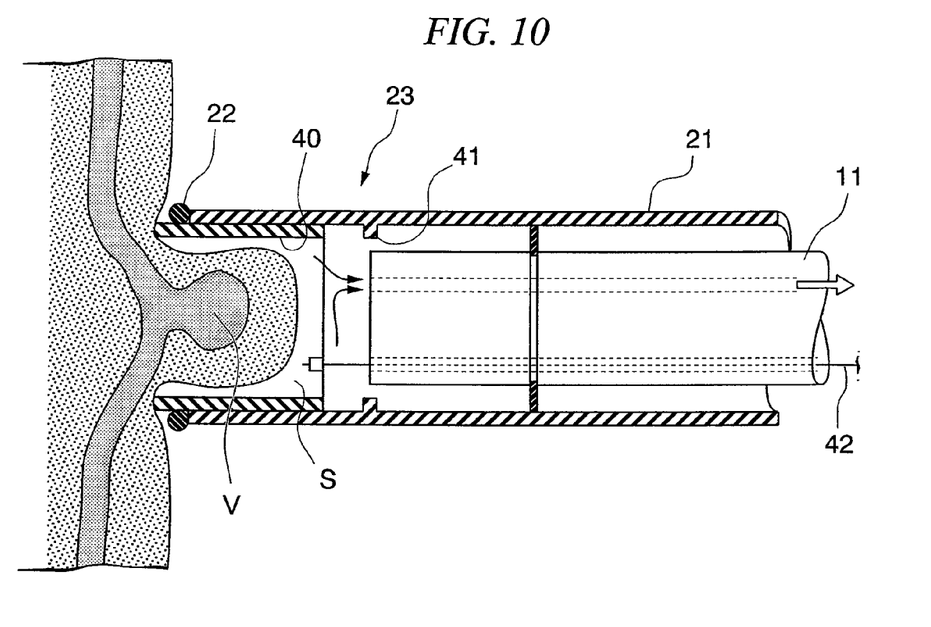
FIG. 10 is a sectional view of chief parts showing a modification of a distal end of an overtube of the embodiment of the invention.
Figure 11:
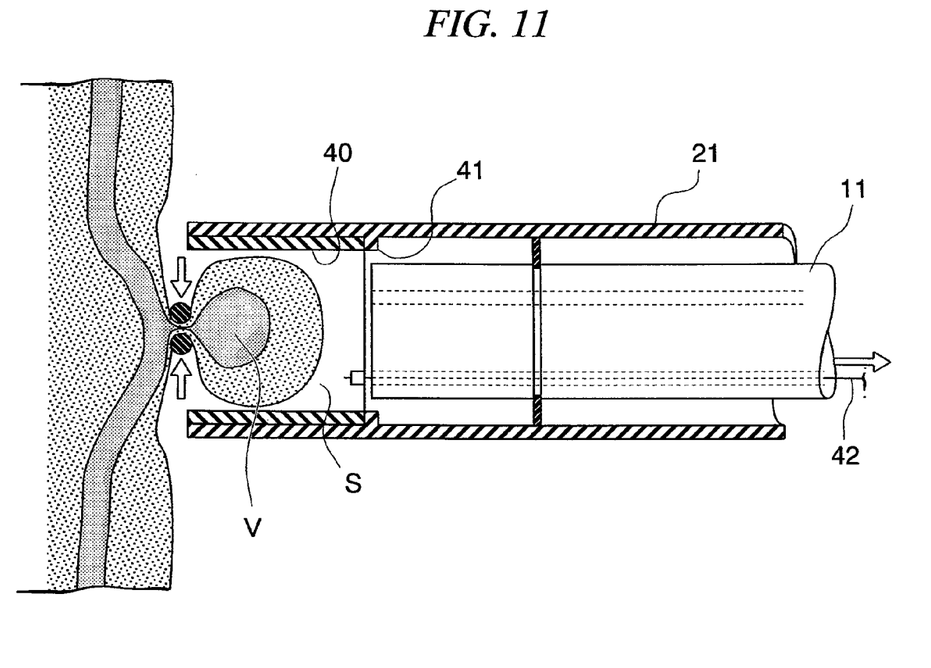
FIG. 11 is a sectional view of chief parts showing a modification of the distal end of the overtube of the embodiment of the invention.

FIGS. 10 and 11 show a modification of the separating mechanism 23 which separates an O-ring 22 for ligation from the tip of the overtube 21.

Here, in the separating mechanism 23, an inner tube 40 is axially slidably fitted into the tip of the overtube 21, and the O-ring 22 for ligation is fitted to the outer periphery of the distal end of the inner tube 40.

Furthermore, an inner flange 41 is formed at an inner peripheral portion of the overtube 21 in a position which has returned slightly to the proximal end from the tip. The inner flange 41 functions as a stopper which abuts on the inner tube 40 and determines the proximal-side movement limit position of the inner tube 40, when the inner tube 40 moves to the proximal side. In addition, the inner flange 41 is formed at a position where the flange abuts the inner tube 40 when the inner tube has moved to the proximal side until the tip of the inner tube 40 is in the same position as the tip of the overtube 21.

Furthermore, the tip of the operation wire 42 is connected to the inner tube 40, and a proximal portion of the operation wire 42 is connected to the wire operation portion, which is not shown, via the channels of the insertion portion.

According to this modification, as shown in FIG. 10, the tip of the inner tube 40 is made to face the varix V. In this state, the tip of the inner tube 40 is pressed against a tissue in a body. Simultaneously, the operation wire 42 is drawn into the proximal side, and the inner tube 40 is forcibly moved to the proximal side to the overtube 21. At this time, the above operation is performed while the tip of the overtube 21 is pressed against a living body tissue so as not to form a gap between the inner tube 40 and the living body tissue.

Here, when the inner tube 40 moves to the proximal side, the O-ring 22 for ligation strikes the tip of the overtube 21 and their movement to the proximal side is regulated. Therefore, the O-ring stops at the tip position of the overtube 21. Also, when the inner tube 40 moves until its proximal end face strikes the inner flange 41 as shown in FIG. 11, the O-ring for ligation cannot remain on the inner tube 40, but is separated from the inner tube, and is hung on a root portion of the varix V.

In addition, in the above example, the inner tube 40 is forcibly moved to the proximal side by the operation wire 42. However, the invention is not limited thereto. For example, when the space S which is surrounded by the tissue in the body, the overtube 21, and the insertion portion 11 of the endoscope and brought into a sealed state is brought into negative pressure by the operation of an air suction mechanism, the inner tube 40 may be moved to the proximal side using the negative pressure.

Figure 12:
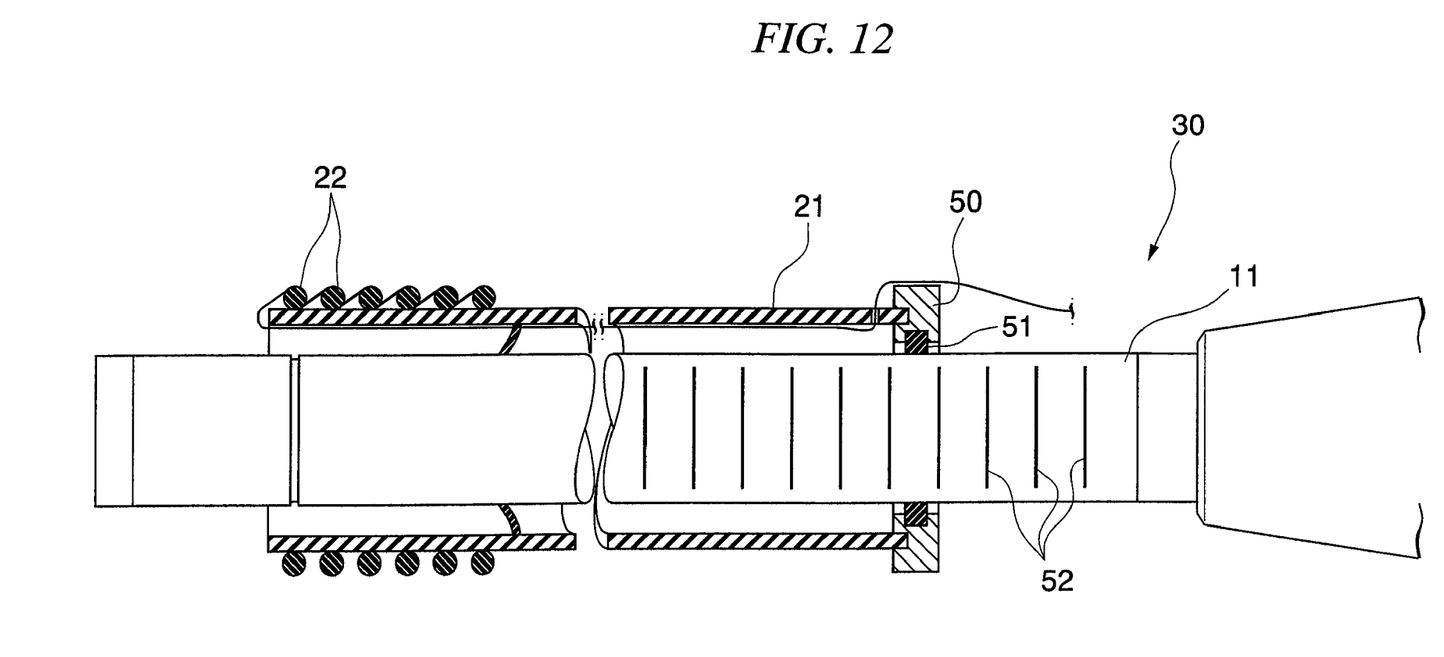
FIG. 12 is a side view obtained when a portion showing a modification of the fixing mechanism of the embodiment of the invention is sectioned.
Figure 13A:
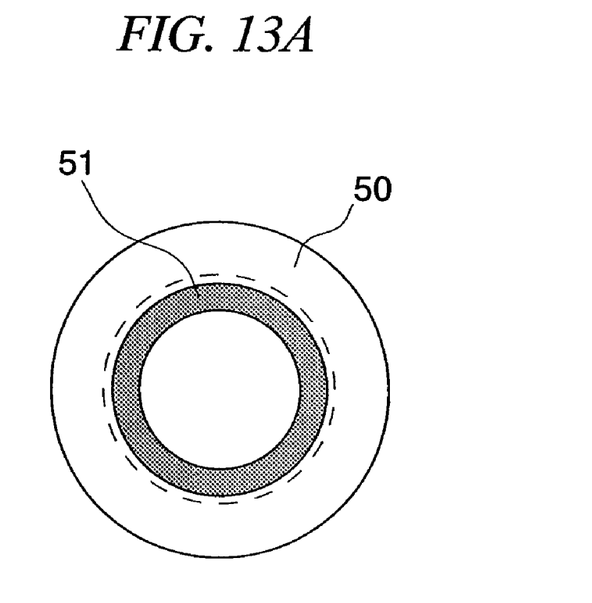
FIG. 13A is a front view of a ring portion of the modification.
Figure 13B:
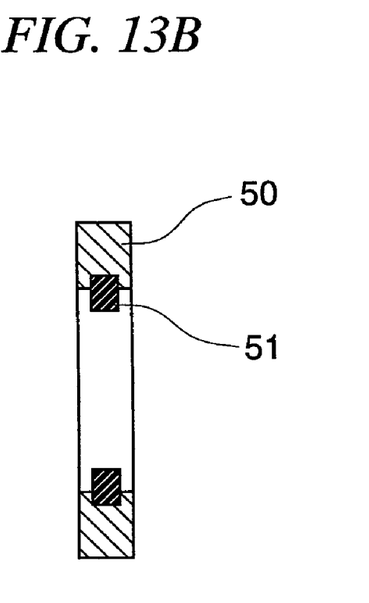
FIG. 13B is a sectional view of the ring portion of the modification.

FIGS. 12, 13A, and 13B show a modification of the fixing mechanism 30 capable of axially fixing the overtube to the insertion portion of the endoscope.

In the fixing mechanism 30 shown herein, a ring portion 50 is attached to the proximal end of the overtube 21, and a rubber ring 51 is attached to an inner periphery of the ring portion 50. The rubber ring 51 is axially slidably fitted to an outer peripheral surface of the insertion portion 11 of the endoscope by its own elasticity. Indexes 52 for indicating in which position the proximal end of the overtube 21 is engaged with the insertion portion 11 are given to the outer peripheral surface of the insertion portion 11 of the endoscope.

According to this modification, the overtube 21 is forcibly moved to the distal side or the proximal side relative to the insertion portion 11 of the endoscope against the frictional force between the rubber ring 51 and the insertion portion 11. This makes it possible to arbitrarily change the relative position of the overtube 21 relative to the insertion portion 11. Thereafter, both can be fixed by the frictional force between the rubber ring 51 and the insertion portion 11.

For this reason, during manipulation, the overtube 21 can be prevented from moving in the axial direction carelessly and disturbing the manipulation, and the position of the overtube relative to the insertion portion 11 can be arbitrarily moved to an optimal position according to a situation.

Figure 14:
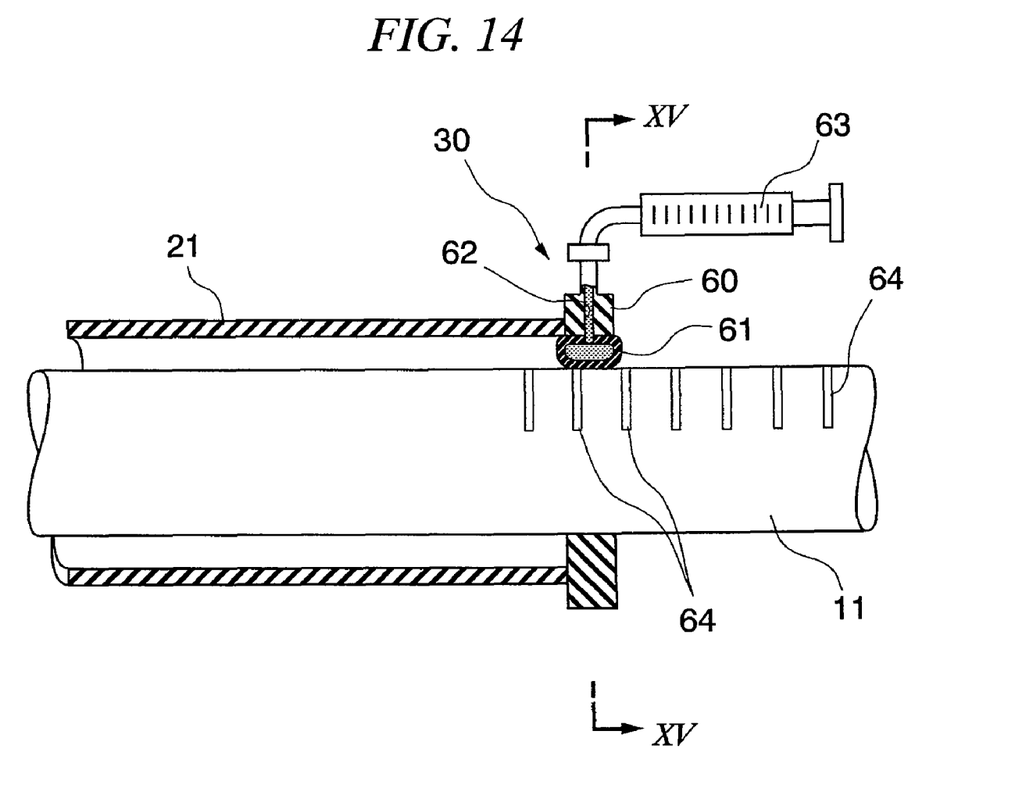
FIG. 14 is a side view obtained when a portion showing another modification of the fixing mechanism of the embodiment of the invention is sectioned.
Figure 15:
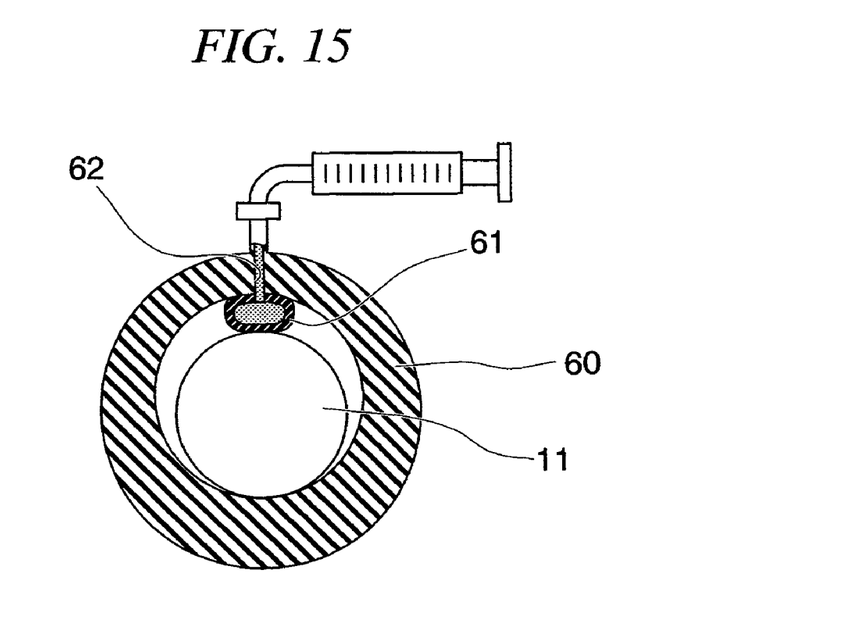
FIG. 15 is a sectional view along a line XV-XV of FIG. 14.

FIGS. 14 and 15 show another modification of the fixing mechanism.

In the fixing mechanism 30 shown herein, a ring portion 60 is attached to the proximal end of the overtube 21, a balloon 61 is attached to an inner periphery of the ring portion 60, and the balloon 61 is connected to an air adjusting means 63, such as a syringe, which is provided outside the ring portion 60, via a communicating path 62 which passes through the ring portion 60. When expanding and contracting operation of the balloon 61 is carried out by the air adjusting means 63, for example, where the diameter-increasing operation of the balloon 61 is carried out, the balloon forcefully strikes the outer peripheral surface of the insertion portion 11 of the endoscope. By the frictional force at that time, the overtube 21 can be fixed to the insertion portion 11 (FIGS. 14 and 15 show a state when the diameter of the balloon 61 is increased). Furthermore, when the overtube 21 is moved in its axial direction relative to the insertion portion 11, the diameter of the balloon 61 is reduced by the air adjusting means 63 so as not to contact the outer peripheral surface of the insertion portion 11. In addition, even in this example, indexes 64 indicating the locking position of the overtube 21 are provided at an outer peripheral surface of an insertion portion 11 of the endoscope.

According to this modification, diameter-reducing operation of the balloon 61 is carried out by the air adjusting means 63, and the overtube 21 is forcibly moved to the distal side or the proximal side to the insertion portion 11 of the endoscope. This makes it possible to move the overtube 21 to an arbitrary position relative to the insertion portion 11, to fix the position.

Figure 16:
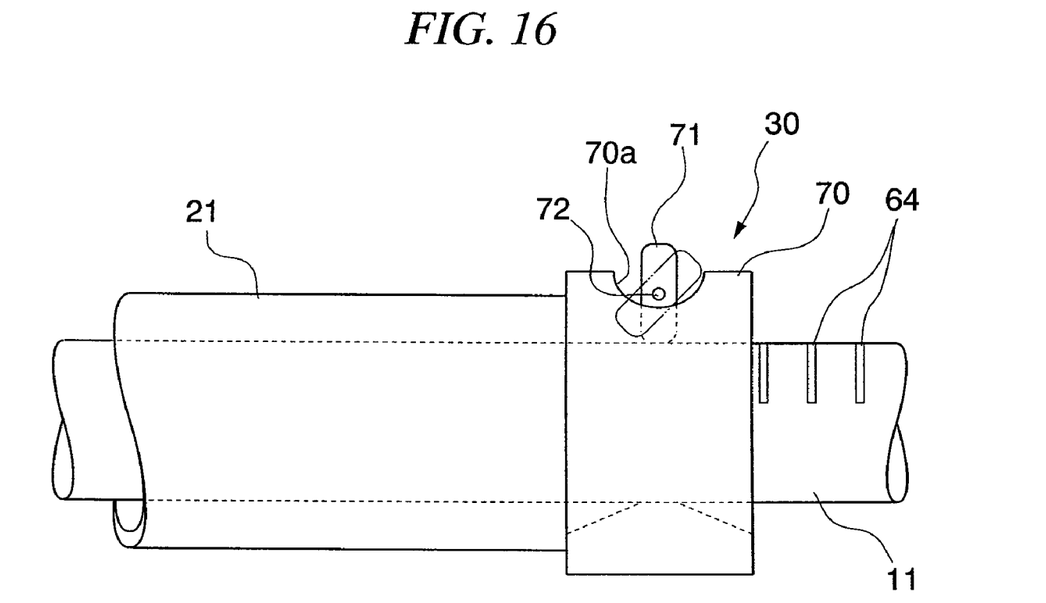
FIG. 16 is a side view obtained when a portion showing another modification of the fixing mechanism of the embodiment of the invention is sectioned.
Figure 17:
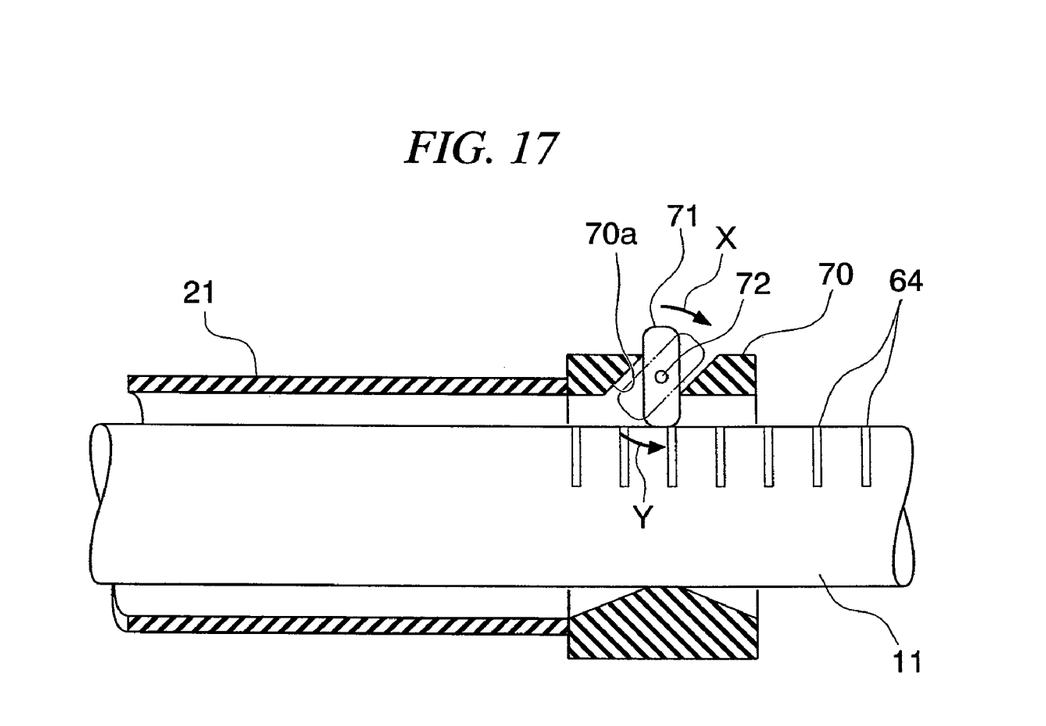
FIG. 17 is a side view showing a portion of the modification in cross-section.

FIGS. 16 and 17 show another modification of the fixing mechanism.

In the fixing mechanism 30 shown herein, a tubular body 70 is coaxially attached to the proximal end of the overtube 21, a lever 71 is disposed in a through hole 70a provided in a wall portion of the tubular body 70, and the lever 71 is rotatably attached via a pin 72 which is disposed so as to be orthogonal to the axial direction of the tubular body 70.

According to this modification, if the lever is titled in the X-direction as shown in FIG. 17, a lower end of the lever 71 rotates so as to retreat from the outer peripheral surface of the insertion portion 11, and the overtube 21 can be moved to an arbitrary position relative to the insertion portion 11. If the lever 71 is rotated and raised after the overtube 21 is moved to a desired position relative to the insertion portion 11, the lower end of the lever 71 forcefully strikes the outer peripheral surface of the insertion portion 11. As a result, the overtube 21 can be fixed to the insertion portion 11 by the frictional force at that time.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A ligation tool for an endoscope comprising:
   a tubular body comprising a screwing portion and an insertion lumen made of a flexible material, wherein the insertion lumen is configured to permit an insertion portion of the endoscope to be inserted therethrough so as to advance and retreat;
   one or more O-rings for ligation attached to a distal end of the tubular body;
   a separating mechanism positioned and configured to separate the O-ring for ligation from a tip of the tubular body; and
   a fixing mechanism comprising a screwed portion positioned to be screwed onto the screwing portion and configured to move axially and to fix the tubular body to the insertion portion of the endoscope by a rotation of the tubular body.

2. The ligation tool for the endoscope according to Claim 1, wherein the fixing mechanism is configured to fix the tubular body to a predetermined position of the insertion portion of the endoscope in advance.

3. The ligation tool for the endoscope according to claim 1, wherein the separating mechanism includes an operation wire locked to the O-ring for ligation at its distal side, and is positioned and configured to be pulled or pushed at its proximal side, thereby separating the O-ring for ligation from the tip of the tubular body.

4. The ligation tool for the endoscope according to claim 3, wherein a proximal portion of the operation wire is connected to a wire operation portion configured to pull or to push the operation wire, and the wire operation portion is detachably attached to an endoscope control portion.

5. An endoscopic ligation system comprising the ligation tool for endoscope according to claim 4, and an endoscope in which an insertion portion is inserted through an insertion lumen of the tubular body so as to advance and retreat.

6. An endoscopic ligation system comprising the ligation tool for endoscope according to claim 3, and an endoscope in which an insertion portion is inserted through an insertion lumen of the tubular body so as to advance and retreat.

7. The ligation tool for the endoscope according to claim 1, wherein a length of the tubular body is shorter than a length of the insertion portion of the endoscope.

8. An endoscopic ligation system comprising the ligation tool for endoscope according to claim 7, and an endoscope in which an insertion portion is inserted through an insertion lumen of the tubular body so as to advance and retreat.

9. The ligation tool for the endoscope according to claim 1, further comprising a seal portion positioned and configured to air-tightly a space formed between the tubular body and the insertion portion of the endoscope into a distal space and a proximal space.

10. The ligation tool for the endoscope according to claim 9, wherein the seal portion is provided between the distal end of the tubular body, and a distal end of the insertion portion of the endoscope.

11. An endoscopic ligation system comprising the ligation tool for endoscope according to claim 10, and an endoscope in which an insertion portion is inserted through an insertion lumen of the tubular body so as to advance and retreat.

12. An endoscopic ligation system comprising the ligation tool for endoscope according to claim 9, and an endoscope in which an insertion portion is inserted through an insertion lumen of the tubular body so as to advance and retreat.

13. An endoscopic ligation system comprising the ligation tool for the endoscope according to claim 1, and an endoscope in which an insertion portion is inserted through an insertion lumen of the tubular body so as to advance and retreat.

14. The ligation tool for the endoscope according to claim 1, wherein the fixing mechanism comprises:
  an inner connector proximally fixed to an outer periphery of the insertion portion and which has the screwed portion at an outer periphery thereof; and
  a ring portion positioned proximally on an outer periphery of the tubular body and which has the screwing portion which is screwed onto the screwed portion.

* * * * *